(12) United States Patent
Guo et al.

(10) Patent No.: US 11,446,057 B2
(45) Date of Patent: Sep. 20, 2022

(54) APPARATUS FOR GUIDING SUBCUTANEOUS PLACEMENT OF PUNCTURE INDWELLING DRAINAGE TUBE

(71) Applicant: SHANDONG PROVINCIAL QIANFOSHAN HOSPITAL, Shandong (CN)

(72) Inventors: Jian Guo, Jinan (CN); Liu Jing, Jinan (CN)

(73) Assignee: SHANDONG PROVINCIAL QIANFOSHAN HOSPITAL, Jinan (CN)

(*) Notice: Subject to any disclaimer, the term of this patent is extended or adjusted under 35 U.S.C. 154(b) by 523 days.

(21) Appl. No.: 16/494,625

(22) PCT Filed: Mar. 29, 2017

(86) PCT No.: PCT/CN2017/078610
§ 371 (c)(1),
(2) Date: Oct. 21, 2019

(87) PCT Pub. No.: WO2018/166000
PCT Pub. Date: Sep. 20, 2018

(65) Prior Publication Data
US 2020/0046405 A1     Feb. 13, 2020

(30) Foreign Application Priority Data

Mar. 14, 2017 (CN) .......................... 201710148968.2

(51) Int. Cl.
*A61B 17/34* (2006.01)
*A61M 27/00* (2006.01)

(52) U.S. Cl.
CPC ...... *A61B 17/3421* (2013.01); *A61B 17/3415* (2013.01); *A61M 27/00* (2013.01);
(Continued)

(58) Field of Classification Search
CPC ............ A61B 17/3403; A61B 17/3415; A61B 17/3417; A61B 17/3421; A61B 17/34;
(Continued)

(56) References Cited

U.S. PATENT DOCUMENTS 3,833,003 A   9/1974  Taricco
5,290,249 A   3/1994  Foster et al.
(Continued)

FOREIGN PATENT DOCUMENTS

CN   201194831 Y   2/2009
CN   102886098 A   1/2013
(Continued)

OTHER PUBLICATIONS

Nov. 16, 2017 Search Report issued in International Patent Application No. PCT/CN2017/078610.

*Primary Examiner* — Nicholas J. Weiss
*Assistant Examiner* — Linnae E. Raymond
(74) *Attorney, Agent, or Firm* — Oliff PLC

(57) ABSTRACT

An apparatus is provided for guiding the subcutaneous placement of a puncture indwelling drainage tube. The apparatus includes a cannula having a first puncture needle core with a first engagement portion that matches a second engagement portion of a second puncture needle core. The apparatus also includes a third puncture needle core having a third engagement portion that matches a fourth engagement portion of a fourth puncture needle core. Front ends of the four puncture needle cores all protrude from a front end of the cannula and four handles all protrude from the rear end.

9 Claims, 9 Drawing Sheets

(52) U.S. Cl.
CPC ............... *A61B 2017/3454* (2013.01); *A61M 2210/1003* (2013.01)

(58) Field of Classification Search
CPC .. A61B 2017/00349; A61B 2017/3445; A61B 2017/3454; A61B 2017/00353; A61B 2017/00358; A61M 25/01; A61M 25/0082; A61M 25/0116; A61M 2210/1003; A61M 27/00
See application file for complete search history.

(56) References Cited

U.S. PATENT DOCUMENTS

| | | | |
|---|---|---|---|
| 2006/0020274 A1* | 1/2006 | Ewers | A61B 17/29 606/148 |
| 2006/0259007 A1 | 11/2006 | McGuckin et al. | |
| 2013/0131688 A1* | 5/2013 | Schwartz | A61B 10/02 606/113 |

FOREIGN PATENT DOCUMENTS

| | | | | |
|---|---|---|---|---|
| CN | 106859741 A | | 6/2017 | |
| JP | H10146391 A | * | 6/1998 | ............. A61B 17/34 |

* cited by examiner

APPARATUS FOR GUIDING SUBCUTANEOUS PLACEMENT OF PUNCTURE INDWELLING DRAINAGE TUBE

FIELD OF THE INVENTION

The present invention relates to the relevant technical field of medical devices, and in particular, to an apparatus for guiding subcutaneous placement of a puncture indwelling drainage tube.

BACKGROUND OF THE INVENTION

At present, indwelling of a drainage tube is clinically achieved in two ways:

1. Incision type (open) placement: the drainage tube is directly placed through an incised wound or placed by opening a subcutaneous tunnel near an incision by means of other instruments.

2. Puncture type (closed) placement: the drainage tube is placed by guidance of a paracentesis trocar or a guide wire introduced after puncture.

Different drainage tube indwelling ways also have their applicable scopes and characteristics in clinical practice.

With the introduction of new materials and new technologies, the second way is more widely used in clinical practice. However, because the puncture channel is linear, and the indwelling drainage tube is also linear between a drainage lumen (gap) and a skin puncture hole, the puncture channel is short and is susceptible to factors such as skin conditions and subcutaneous tissue thickness. As time goes on, around-drainage tube exudation, loosening of the drainage tube, and even retrograde infection easily occur, especially for patients with severe obesity or weight loss.

For example, the indwelling time of a common neurosurgical lumbar drainage tube is generally 2-3 weeks. When a severely obese patient carries out a turning over activity or carries out other activities, the drainage tube is prone to movement relative to the skin or to loosening caused by tension due to the thick subcutaneous fat layer. For a patient with obvious weight loss, cerebrospinal fluid is prone to exudation along the gap between the drainage tube and the puncture hole, and even the exudation of cerebrospinal fluid begins during placement, even if the skin around the puncture hole is sutured.

The above two cases cause difficulty in maintenance of the drainage tube, poor drainage treatment effect, and even increase in risk of retrograde infection. Even if puncture and placement are performed again in the midway, including replacement of the lumbar puncture gap, the above defects still exist, which ultimately affects the treatment effect and even causes infection. The implementation of lumbar drainage is also seriously affected for those with poor skin conditions in the lower back (e.g., adjacent superficial inflammation, etc.).

SUMMARY OF THE INVENTION

In order to solve the problems of the prior art, the present invention provides an apparatus for guiding subcutaneous placement of a puncture indwelling drainage tube. By designing a completely new arrangement for the apparatus, after the head segment (anterior segment) of a drainage tube has entered the target cavity (gap), the tail (proximal segment) travels a certain distance in the body and then is led out of the body, which essentially solves the problem that the indwelling drainage tube due to the existing linear puncture is prone to loosening and around-drainage tube exudation which might increase the risk of infection.

In order to achieve the above objective, the present invention adopts the following technical solution:

An apparatus for guiding subcutaneous placement of a puncture indwelling drainage tube, including:

a cannula in which a first puncture needle core, a second puncture needle core, a third puncture needle core and a fourth puncture needle core are arranged;

the front portion of the first puncture needle core is a tip, the first puncture needle core has a first engagement portion, and the tail portion of the first puncture needle core is provided with a first handle;

the front end of the second puncture needle core has a second engagement portion that matches the first engagement portion of the first puncture needle core, and the tail portion of the second puncture needle core is provided with a second handle;

the front portion of the third puncture needle core is a tip, the third puncture needle core has a third engagement portion, and the tail portion of the third puncture needle core has is provided with a third handle;

the front end of the fourth puncture needle core has a fourth engagement portion that matches the third engagement portion of the third puncture needle core, and the tail portion of the fourth puncture needle core is provided with a fourth handle;

the front ends of the four puncture needle cores protrude from the front end of the cannula; the four handles protrude from the rear end of the cannula. In addition, the four puncture needle cores protrude from the rear end of the puncture cannula in the same length and can be combined together.

With the above arrangement, the four puncture needle cores are engaged together to expose the front end of the cannula to be conical. The first puncture needle core and the second puncture needle core constitute an upper half cone, and the third puncture needle core and the fourth puncture needle core constitute a lower half cone.

Preferably, the front ends of the first puncture needle core, the second puncture needle core, the third puncture needle core, and the fourth puncture needle core form a conical arrangement.

Preferably, the cannula is provided with a holding portion.

Preferably, the first engagement portion includes a first curved surface within the first puncture needle core and a second curved surface on a side of the first puncture needle core, the first curved surface of the first puncture needle core presents a cambered edge extruded toward the left end (head) when top-viewed, and the second curved surface presents a cambered edge extruded toward the right side (tail) when viewed from the side, so that the first puncture needle core can be in smooth contact with the drainage tube without an acute angle.

Preferably, the second engagement portion includes a third curved surface within the second puncture needle core and a fourth curved surface on a side of the second puncture needle core, the third curved surface of the second puncture needle core presents a cambered edge extruded toward the left side when top-viewed, and the fourth curved surface presents a cambered edge extruded toward the right side when viewed from the side. The second engagement portion completely matches the first engagement portion, and the two engagement portions are closely engaged with each other to avoid embedding of soft tissues during puncture.

Preferably, the third engagement portion is of a planar arrangement, and the main body of the third puncture needle core has a sector-shaped cross section.

Preferably, the fourth engagement portion is of a planar arrangement, and the main body of the fourth puncture needle core has a sector-annular-shaped cross section. After the third puncture needle core and the fourth puncture needle core are integrally and closely attached to each other, the main bodies of the third puncture needle core and the fourth puncture needle core form a sector-annular-shaped sectional arrangement having a 180° central angle, so that the centripetal sides of the main bodies of the third puncture needle core and the fourth puncture needle core together form a groove capable of accommodating the drainage tube.

At the same time, the distance between the interface facing the transition of the first and second engagement portions on an operating side of the second puncture needle core and the conical tip is equal to the distance between the fourth engagement portion of the fourth puncture needle core and the conical tip, thereby ensuring that a puncture needle can simultaneously enter positions between the upper and lower engagement portions (i.e., between the first and second engagement portions, and between the third and fourth engagement portions) when the apparatus is used.

Preferably, the front centripetal side of the fourth puncture needle core has a guiding cambered surface.

The present invention also provides another apparatus for guiding subcutaneous placement of a puncture indwelling drainage tube, including:

a first puncture needle core and a second puncture needle core;

the front portion of the first puncture needle core is a tip, the first puncture needle core has a first engagement portion, and the tail portion of the first puncture needle core is provided with a first handle;

the front end of the second puncture needle core has a second engagement portion that matches the first engagement portion of the first puncture needle core, and the tail portion of the second puncture needle core is provided with a second handle.

Preferably, the first engagement portion includes a first curved surface within the first puncture needle core and a second curved surface on a side of the first puncture needle core, the first curved surface of the first puncture needle core presents a cambered edge extruded toward the left side when top-viewed, and the second curved surface presents a cambered edge extruded toward the right side when viewed from the left side, so that the first puncture needle core can be in smooth contact with the drainage tube without an acute angle.

Preferably, the second engagement portion includes a third curved surface within the second puncture needle core and a fourth curved surface on a side of the second puncture needle core, the third curved surface of the second puncture needle core presents a cambered edge extruded toward the left side when viewed from top to bottom, and the fourth curved surface presents a cambered edge extruded toward the right side when viewed from the side. The second engagement portion completely matches the first engagement portion, and the two engagement portions are closely engaged with each other to avoid embedding of soft tissues during puncture.

Compared with the prior art, the present invention has the following advantages:

(1) Depending on the cooperation of the cannula and the four puncture needle cores, the drainage tube can be laterally pulled for an obese patient, and the drainage tube travels a certain distance and then gets out of the skin, thereby extends the subcutaneous length of the drainage tube, and effectively reduces the risks of loosening of the drainage tube, around-drainage tube exudation of the drainage tube and even retrograde infection caused by linear puncture tube placement in the prior art.

(2) Depending on cooperation of the first puncture needle core and the second puncture needle core, the first and second puncture needle cores can be operated separately for a slim patient, the first puncture needle core and the second puncture needle core are combined into an integral semi-conical puncture arrangement. During the operation, after the first puncture needle core pulls the drainage tube away from the vertical puncture channel, the proximal subcutaneous part of the front side of the drainage tube can be pressed by hand to fix the anterior segment, and the drainage tube is continuously laterally pulled to get out of the skin, thereby extends the subcutaneous length of the drainage tube, and effectively reduces the risks of around-drainage tube exudation, loosening of the drainage tube and even retrograde infection caused by linear puncture tube placement in the prior art.

BRIEF DESCRIPTION OF THE DRAWINGS

The accompanying drawings constituting a part of the present application are used for providing a further understanding of the present application, and the schematic embodiments of the present application and the descriptions thereof are used for interpreting the present application, rather than constituting improper limitations to the present application.

FIG. 24 is a schematic view showing a state of the drainage tube after subcutaneous placement; In which:

Figure 1:
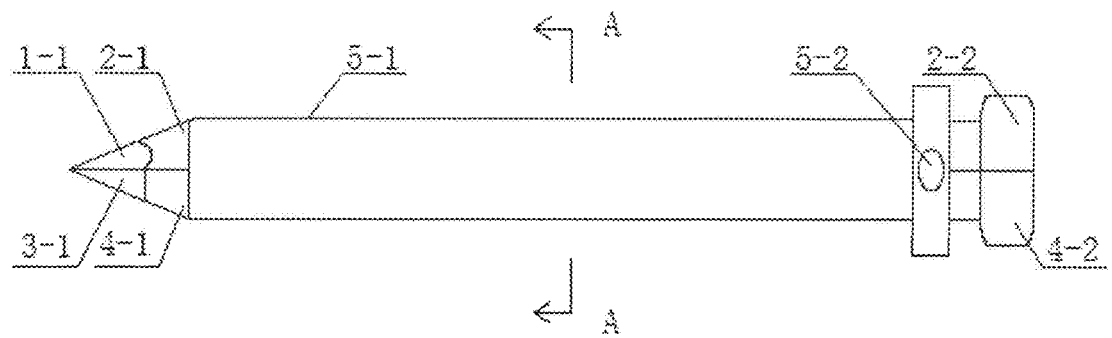
FIG. 1 is a left view of Embodiment 1 of the present invention.
Figure 2:
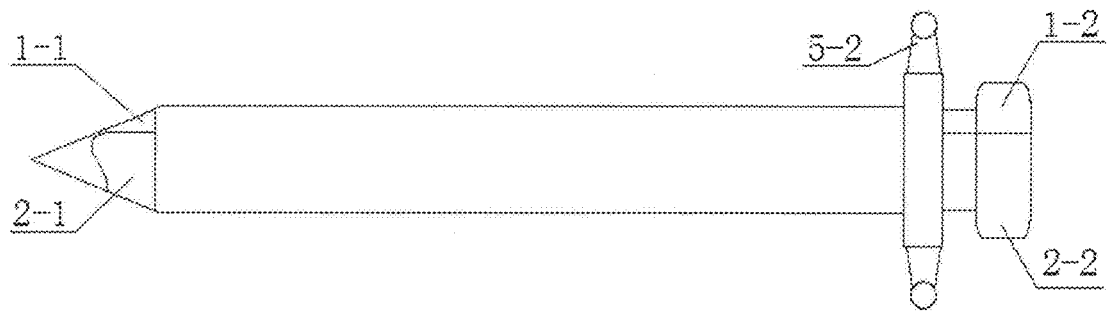
FIG. 2 is a top view of Embodiment 1 of the present invention.
Figure 3:
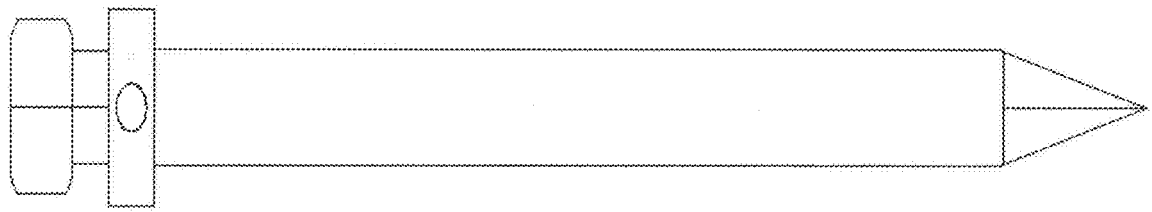
FIG. 3 is a right view of Embodiment 1 of the present invention.
Figure 4:
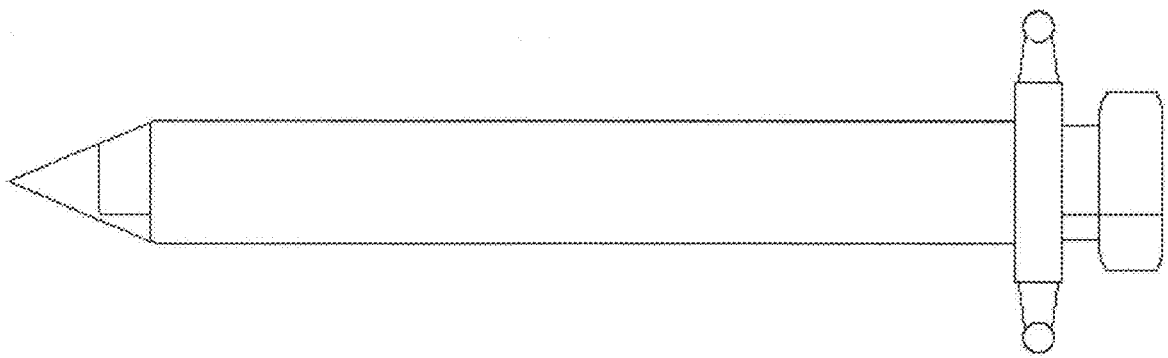
FIG. 4 is a bottom view of Embodiment 1 of the present invention.
Figure 5:
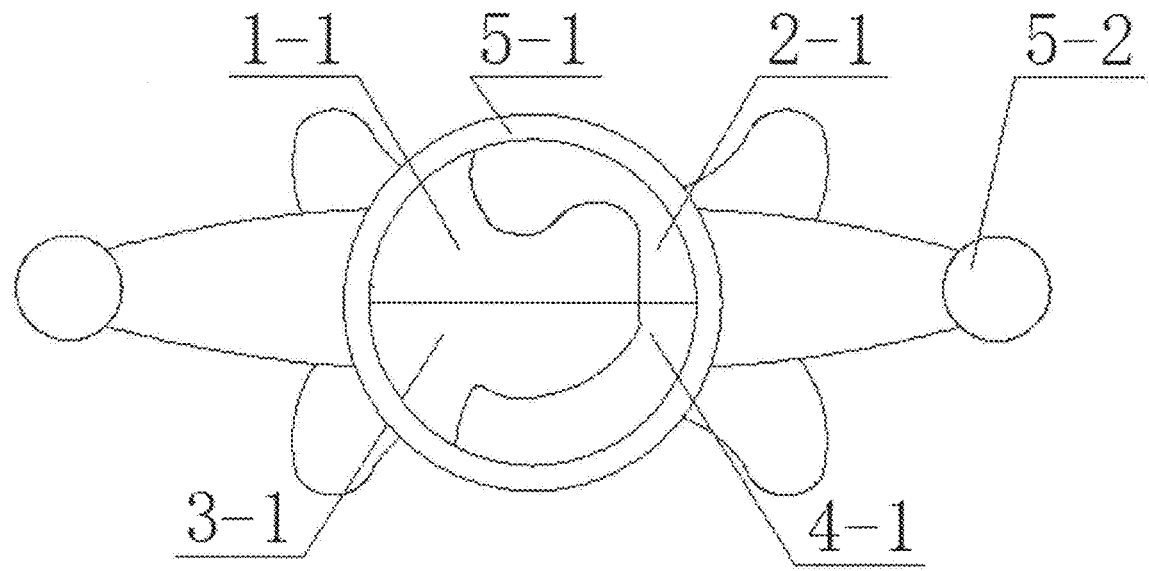
FIG. 5 is a front view of Embodiment 1 of the present invention.
Figure 6:
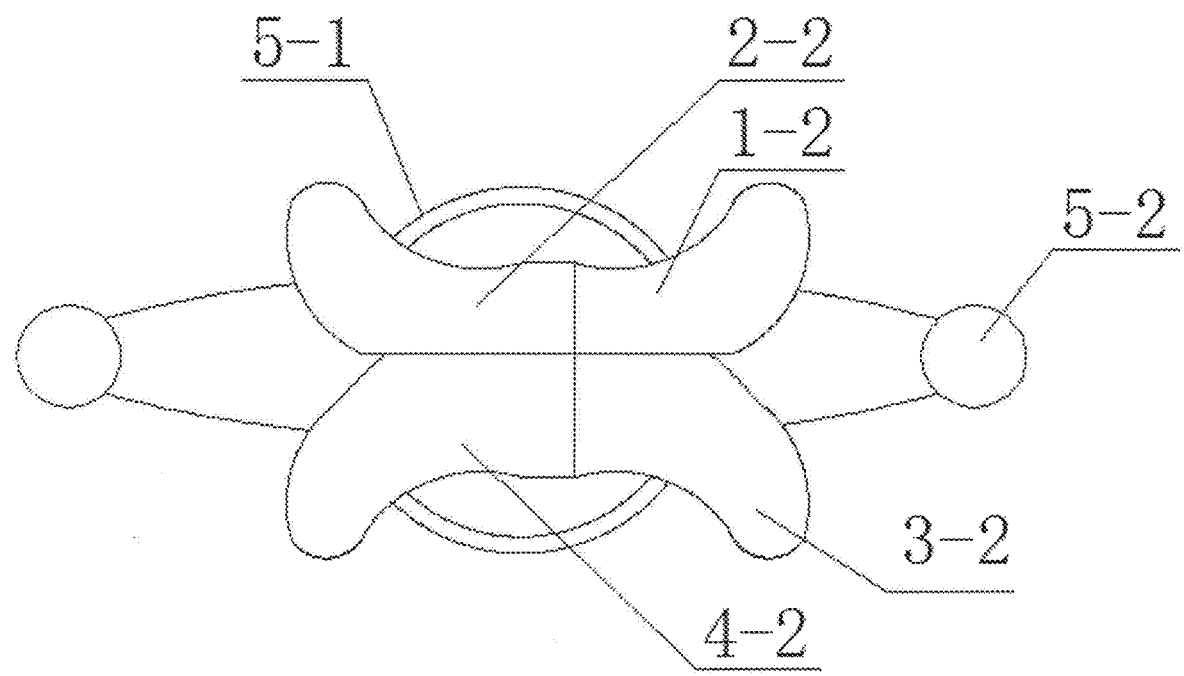
FIG. 6 is a rear view of Embodiment 1 of the present invention.
Figure 7:
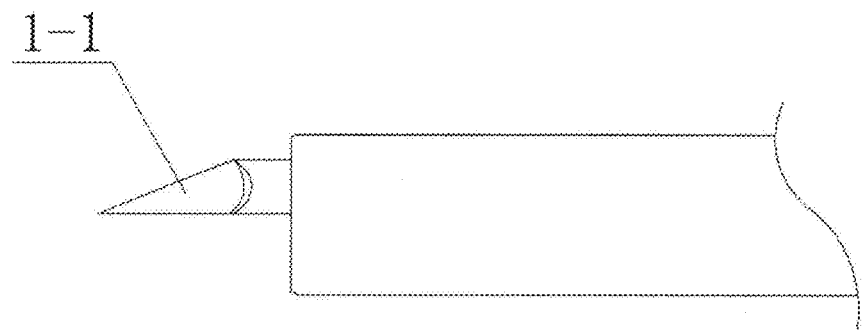
FIG. 7 is a left view of a first puncture needle core in a cannula according to Embodiment 1 of the present invention.
Figure 8:
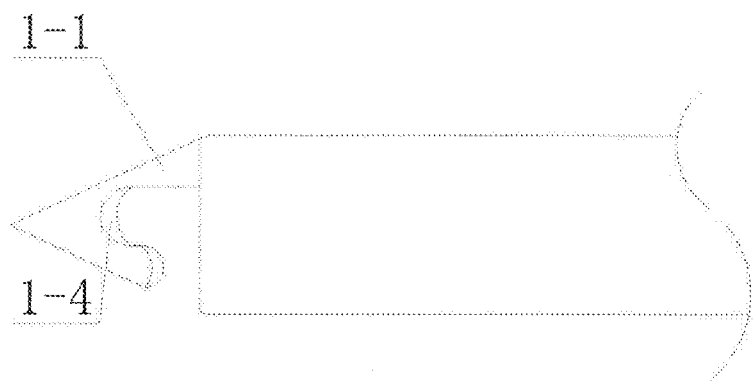
FIG. 8 is a top view of the first puncture needle core in the cannula according to Embodiment 1 of the present invention.
Figure 9:
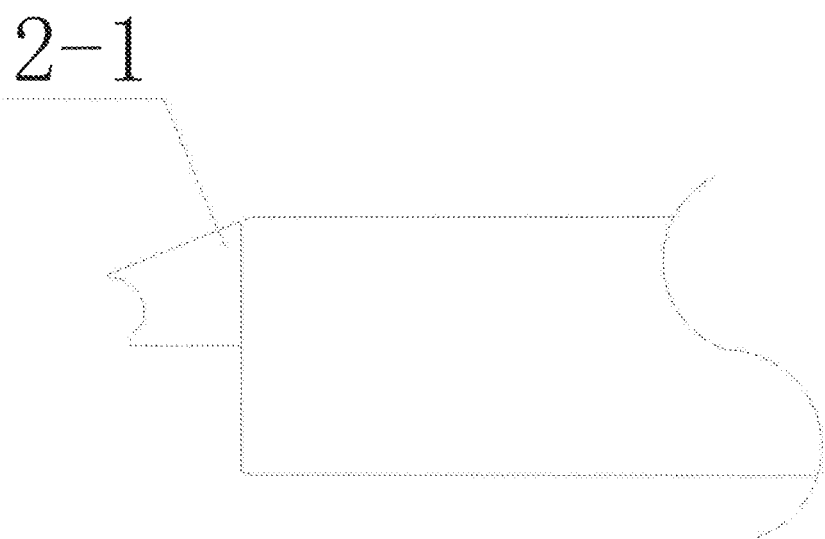
FIG. 9 is a left view of a second puncture needle core in the cannula according to Embodiment 1 of the present invention.
Figure 10:
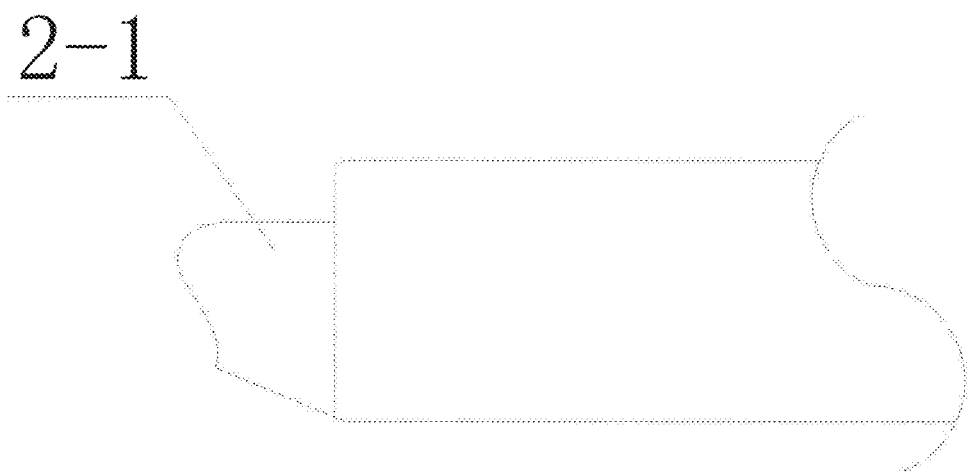
FIG. 10 is a top view of the second puncture needle core in the cannula according to Embodiment 1 of the present invention.
Figure 11:
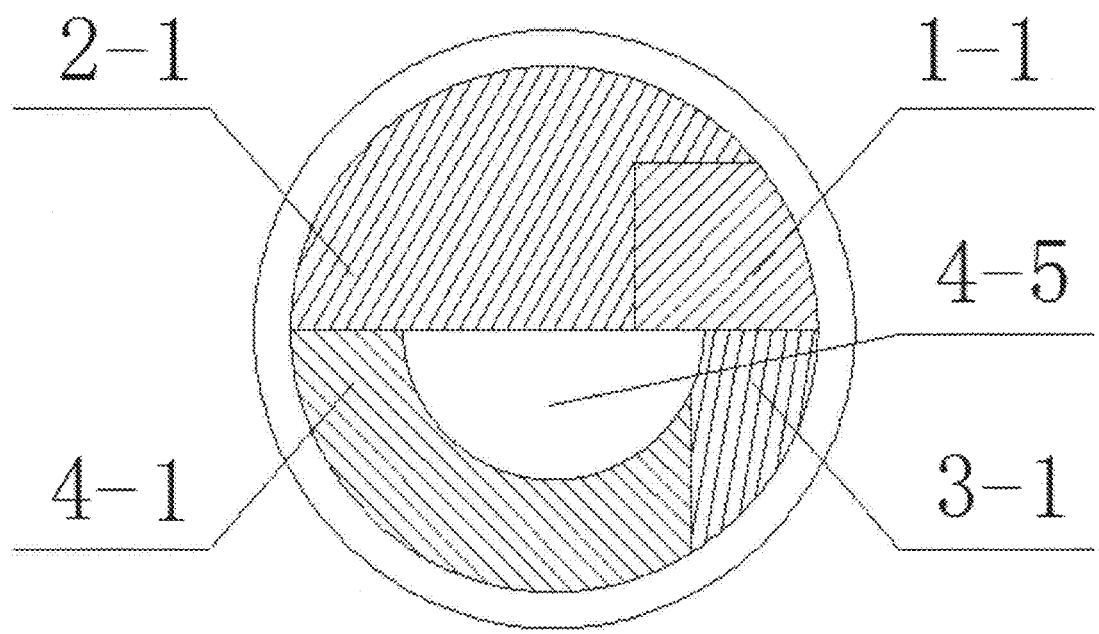
FIG. 11 is a cross-sectional view along A-A of FIG. 1.
Figure 12:
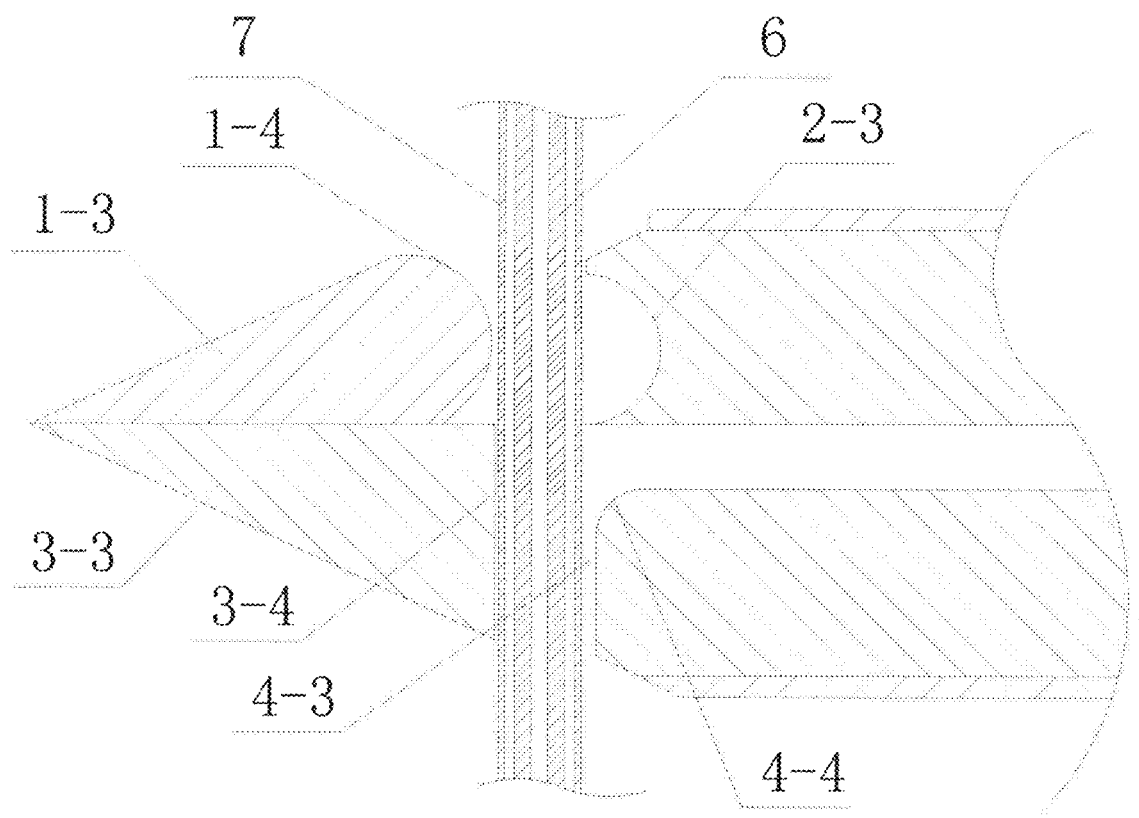
FIG. 12 is a schematic view showing a state of an apparatus according to Embodiment 1 of the present invention when a puncture needle is caught in upper and lower engagement openings.
Figure 13:
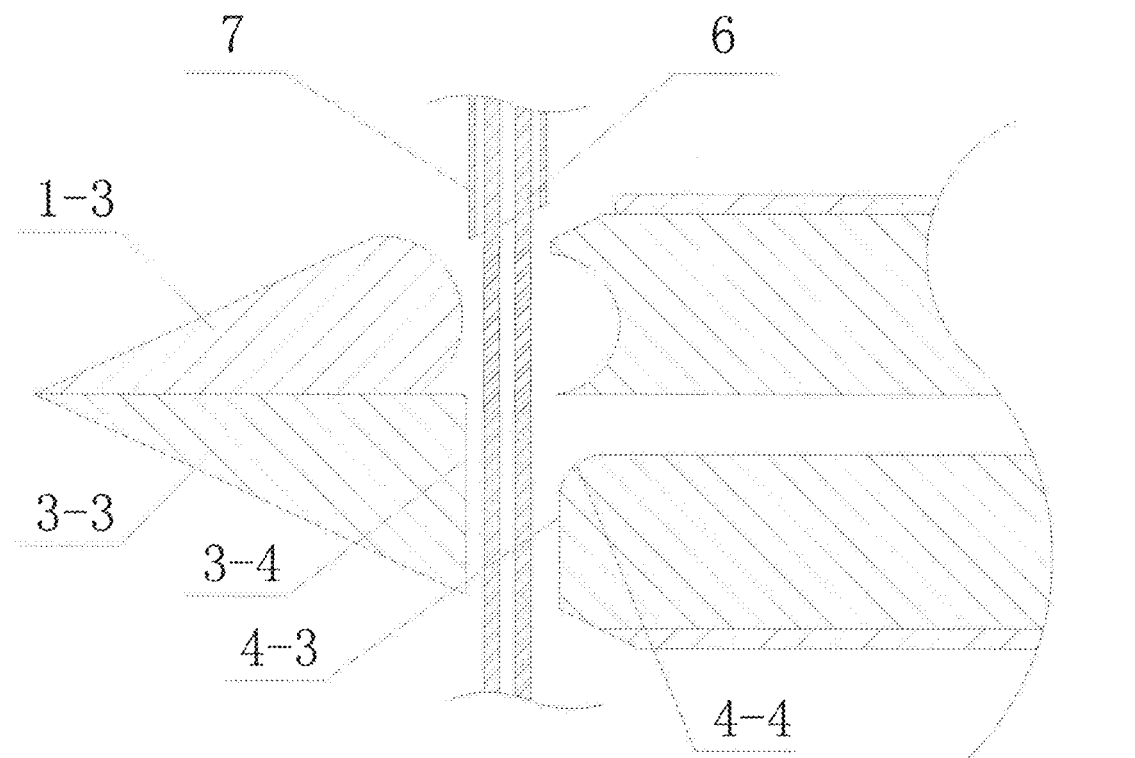
FIG. 13 is a schematic view showing a state of the apparatus according to Embodiment 1 of the present invention when the puncture needle is retracted while the head segment of the drainage tube is kept immobile.
Figure 14:
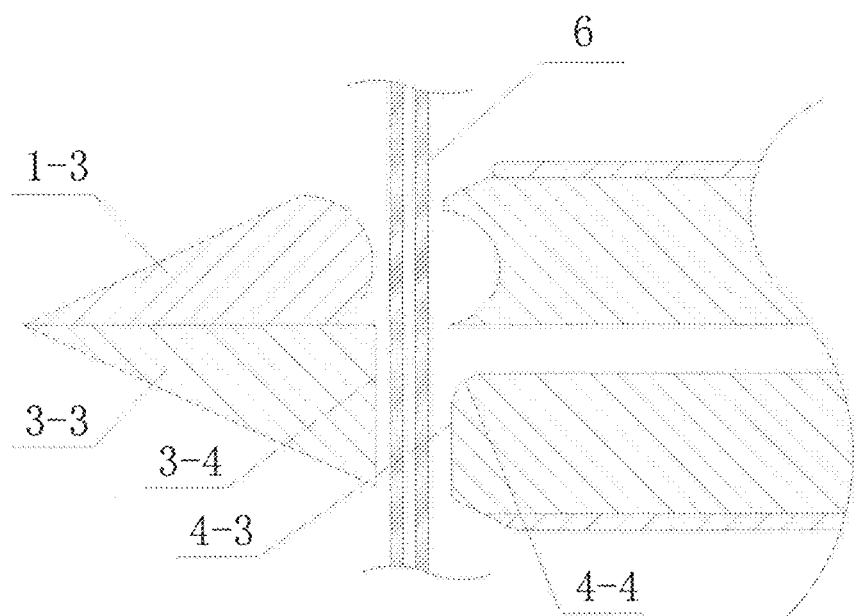
FIG. 14 is a schematic view showing a state of the apparatus according to Embodiment 1 of the present invention after the puncture needle is completely retracted.
Figure 15:
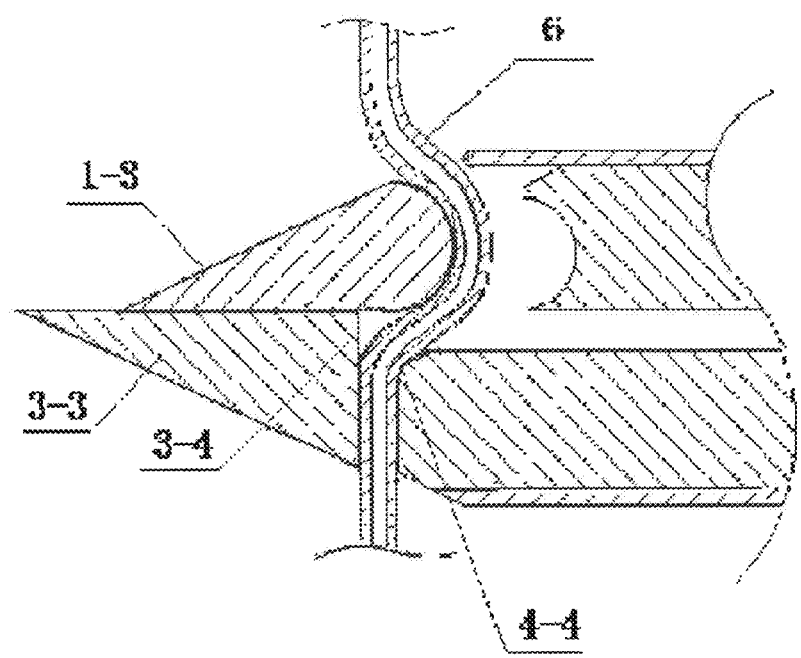
FIG. 15 is a schematic view showing a state of the apparatus according to Embodiment 1 of the present invention when the drainage tube is laterally hooked and pulled.
Figure 16:
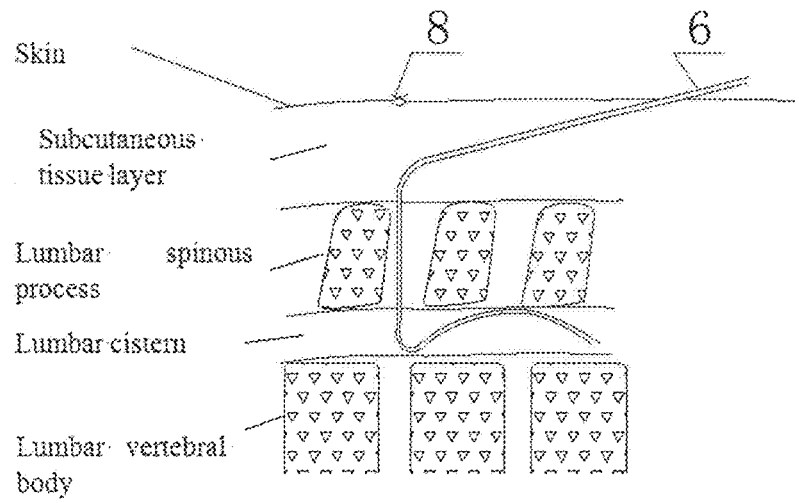
FIG. 16 is a schematic view showing a state of the apparatus according to Embodiment 1 of the present invention after the drainage tube is led out.

First puncture needle core 1-1, first handle 1-2, first tip 1-3, first engagement portion 1-4;

Second puncture needle core 2-1, second handle 2-2, second engagement portion 2-3;

Third puncture needle core 3-1, third handle 3-2, third tip 3-3, third engagement portion 3-4;

Fourth puncture needle core 4-1, fourth handle 4-2, fourth engagement portion 4-3, guiding cambered surface 4-4, groove 4-5;

Cannula 5-1, holding portion 5-2;

Drainage tube 6;

Puncture needle 7;

Suture line 8.

DETAILED DESCRIPTION OF EMBODIMENTS

It should be pointed out that the following detailed descriptions are all exemplary and aim to further illustrate the present application. Unless otherwise specified, all technical and scientific terms used herein have the same meanings generally understood by those of ordinary skilled in the art of the present application.

It should be noted that the terms used herein are merely for describing specific embodiments, but are not intended to limit exemplary embodiments according to the present application. As used herein, unless otherwise explicitly pointed out by the context, the singular form is also intended to include the plural form. In addition, it should also be understood that when the terms "include" and/or "comprise" are used in the specification, they indicate features, steps, operations, devices, components and/or combination thereof.

As described in the background, in the prior art, the indwelling drainage tube due to linear puncture is prone to various problems, for example, around-drainage tube exudation, loosening of the drainage tube and even retrograde infection are prone to occurrence as time goes on after the linear puncture. In order to solve these problems, the apparatus of the present invention is designed.

Embodiment 1

An apparatus for guiding subcutaneous placement of a puncture indwelling drainage tube is shown in FIG. 1-11, including:

a cannula 5-1 in which a first puncture needle core 1-1, a second puncture needle core 2-1, a third puncture needle core 3-1, and a fourth puncture needle core 4-1 are arranged;

the front portion of the first puncture needle core 1-1 is a first tip 1-3, the first puncture needle core 1-1 has a first engagement portion 1-4, and the tail portion of the first puncture needle core is provided with a first handle 1-2;

the front end of the second puncture needle core 2-1 has a second engagement portion 2-3 that matches the first engagement portion 1-4 of the first puncture needle core, the tail portion of the second puncture needle core 2-1 is provided with a second handle 2-2, and the second puncture needle core 2-1 has a second tip;

the front portion of the third puncture needle core 3-1 is a third tip 3-3, the third puncture needle core 3-1 has a third engagement portion 3-4, and the tail portion of the third puncture needle core 3-1 is provided with a third handle 3-2;

the front end of the fourth puncture needle core 4-1 has a fourth engagement portion 4-3 that matches the third engagement portion 3-4 of the third puncture needle core 3-1, the tail portion of the fourth puncture needle core 4-1 is provided with a fourth handle 4-2, and the fourth puncture needle core 4-1 has a fourth tip;

the front ends of the four puncture needle cores protrude from the front end of the cannula 5-1; the four handles protrude from the rear end of the cannula 5-1.

As a preferred arrangement, the front ends of the first puncture needle core 1-1, the second puncture needle core 2-1, the third puncture needle core 3-1 and the fourth puncture needle core 4-1 form a conical arrangement, and the main bodies of the needle cores form a cylindrical arrangement, so that the apparatus facilitates puncture. Generally, the first puncture needle core 1-1 and the second puncture needle core 2-1 are the upper half in the cannula 5-1, and the third puncture needle core 3-1 and the fourth puncture needle core 4-1 are the lower half in the cannula 5-1.

The cannula 5-1 is provided with a holding portion 5-2, which facilitates holding during puncture. The first engagement portion 1-4 of the first puncture needle core 1-1 is a composite curved surface, the second engagement portion 2-3 of the second puncture needle core 2-1 is also a composite curved surface, and the engagement portion between the first puncture needle core 1-1 and the second puncture needle core 2-1 can well accommodate a puncture needle 7 after opened. After the second engagement portion 2-3 of the second puncture needle core 2-1 is closely attached to the first engagement portion 1-4 of the first puncture needle core 1-1, the first puncture needle core 1-1 and the second puncture needle core 2-1 form an axisymmetric arrangement.

After the fourth engagement portion 3 of the fourth puncture needle core 4-1 is engaged with the third engagement portion 3-4 of the third puncture needle core 3-1, the third puncture needle core 3-1 and the fourth puncture needle core 4-1 form an axisymmetric arrangement.

The upper surface of the front end of the fourth puncture needle core 4-1 has a guiding cambered surface 4-4, which can play a certain guiding role when a drainage tube 6 is clamped and fixed by the fourth puncture needle core 4-1 and the third puncture needle core 3-1 and hooked and pulled by the puncture needle core 1-1. The third puncture needle core 3-1 and the fourth puncture needle core 4-1 are engaged to form a sector-annular-shaped sectional arrangement having a semi-conical front end and a body cross section of a 180° central angle, so that the interiors of the third puncture needle core 3-1 and the fourth puncture needle core 4-1 together form a groove 4-5 capable of accommodating the drainage tube 6.

As shown in FIGS. 12-15, the surgical procedure of this apparatus is as follows:

This operation is more suitable for an obese patient, and requires the cannula 5-1, the first puncture needle core 1-1, the second puncture needle core 2-1, the third puncture needle core 3-1 and the fourth puncture needle core 4-1.

After the puncture needle punctures a target drainage lumen or gap successfully and the drainage tube 6 is placed to a sufficient depth through the puncture needle 7, the puncture needle 7 and the drainage tube 6 are held still, and the apparatus punctures from a target position for leading the drainage tube 6 out to the puncture needle (the distance between two skin puncture holes is measured in advance to evaluate the puncture depth of the apparatus, and the subcutaneous length of the drainage tube); the orientation of the apparatus is finely adjusted when the tips of the four needle cores touch the puncture needle 7, so that the conical portion of the tip of the apparatus slides closely along the right side of the puncture needle 7; and the second puncture needle core 2-1 and the fourth puncture needle core 4-1 are retracted to enlarge the engagement gap between the first puncture needle core 1-1 and the second puncture needle core 2-1 and the engagement gap between the third puncture needle core 3-1 and the fourth puncture needle core 4-1. When the front end of the apparatus slides to the puncture needle, the jamming feeling is touched at the engagement opening. At this time, the second puncture needle core 2-1 and the fourth puncture needle core 4-1 are appropriately retracted to adjust the engagement gaps between the first puncture needle core 1-1 and the second puncture needle core 2-1 and between the third puncture needle core 3-1 and the fourth puncture needle core 4-1, and the puncture needle is completely engaged in the engagement openings between the first puncture needle core 1-1 and the second puncture needle core 2-1 and between the third puncture needle core 3-1 and the fourth puncture needle core 4-1. Subsequently, the puncture needle 7 is retracted while the depth of the drainage tube 6 is kept constant. If no jamming feeling is generated after the conical front end of the apparatus slides completely over the puncture needle, the position of the engagement opening may have been missed or the upper and lower engagement openings are inconsistent (since the engagement openings between 1-1 and 2-1 and between 3-1 and 4-1 are too small or staggered, the upper and lower engagement openings are inconsistent), the puncture needle cores 2-1 and 4-1 may be appropriately retracted to enlarge the engagement opening, so that the apparatus slides front and back close to the puncture needle.

After it is confirmed that the puncture needle is in the upper and lower engagement openings (engagement openings between 1-1 and 2-1 and between 3-1 and 4-1) of the apparatus, the puncture needle is retracted while the drainage tube and the apparatus are kept fixed, the fourth puncture needle core 4-1 is appropriately pushed forward, and the engagement gap between the third puncture needle core 3-1 and the fourth puncture needle core 4-1 is adjusted to clamp the drainage tube 6. The second puncture needle core 2-1 is retracted out, the first puncture needle core 1-1 is pulled backward, the drainage tube 6 is hooked and pulled by the hook-shaped engagement opening of the first puncture needle core 1-1 and extracted through the tail hole of the cannula 5-1, and the tail segment (in vitro part) of the drainage tube 6 can be pushed into the body through a vertical puncture hole in the pulling process to reduce the pulling resistance of the first puncture needle core 1-1. After the drainage tube 6 is exposed through a tail opening of the cannula of the apparatus, the drainage tube 6 is steadily pulled by hand till the tail end of the drainage tube 6 is exposed to the outside of the body. It should be noted that the tension between the third puncture needle core 3-1 and the fourth puncture needle core 4-1 is maintained during the pulling of the drainage tube 6 to prevent the head segment of the drainage tube 6 from being shifted by pulling. When the drainage tube 6 is pulled by hand, the head segment and the tail segment of the drainage tube 6 should be distinguished. The delivery of the drainage tube into the body through the vertical puncture hole by pulling the tail segment junction of the drainage tube 6 can reduce the resistance of pulling the drainage tube and shorten the time.

The fourth puncture needle core 4-1 is retracted to release the pressing on the drainage tube 6, the third puncture needle core 3-1 is appropriately pushed forward, then rotated clockwise and retracted to avoid pulling the drainage tube 6, the cannula 5-1 is retracted subsequently, it should be noted to maintain the position of the drainage tube 6 at the same time, and whether a suture line 8 is required for suturing is finally determined according to the condition of the puncture hole left by the vertical puncture. For the state after the surgery, reference may be made to FIG. 14.

During the retraction of the cannula 5-1, the third puncture needle core 3-1 and the fourth puncture needle 4-1, it should be further noted that:

(1) The fourth puncture needle core 4-1 is retracted out to release the pressing on the drainage tube 6, and the third puncture needle core 3-1 is appropriately pushed forward and then rotated 180° clockwise, so that its engagement portion is away from the drainage tube 6 and then is steadily retracted to avoid pulling the drainage tube 6, causing the head segment of the drainage tube 6 to be shifted by pulling;

(2) When the cannula 5-1 is retracted, the drainage tube 6 is appropriately returned to reduce the tension between the drainage tube 6 and perivascular soft tissues.

The apparatus provided in this embodiment is suitable for all patients, and is more meaningful for obese patients. For a vertical puncture hole, suturing is not required according to the situation.

Refer to FIGS. 19-24 for the application states of the apparatus during actual surgery.

With the above arrangement, after the head segment of the drainage tube 6 has been placed into a target lumen or gap by vertical puncture, the drainage tube 6 can be extracted from a side skin puncture hole by subcutaneous side pulling, which obviously extends the travel distance of the drainage tube in the body, reduces the loosening caused by relative movement between the drainage tube and the skin and subcutaneous soft tissues during the activities such as turning over, and thickens the anti-infection barrier, thereby reduces the problems of around-drainage tube exudation, loosening of the drainage tube and even retrograde infection after tube placement by existing linear puncture. The care of patients with indwelling drainage tubes is improved, the chance of infection is reduced, and the time during which the drainage tube can maintain an effective working condition inside the body is ultimately prolonged to improve the treatment effect.

Embodiment 2

Figure 17:
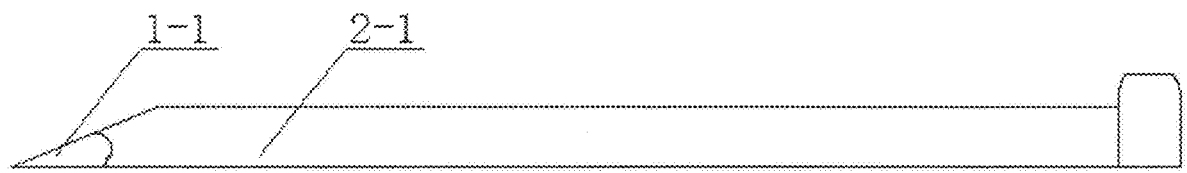
FIG. 17 is a left view of Embodiment 2 of the present invention.
Figure 18:
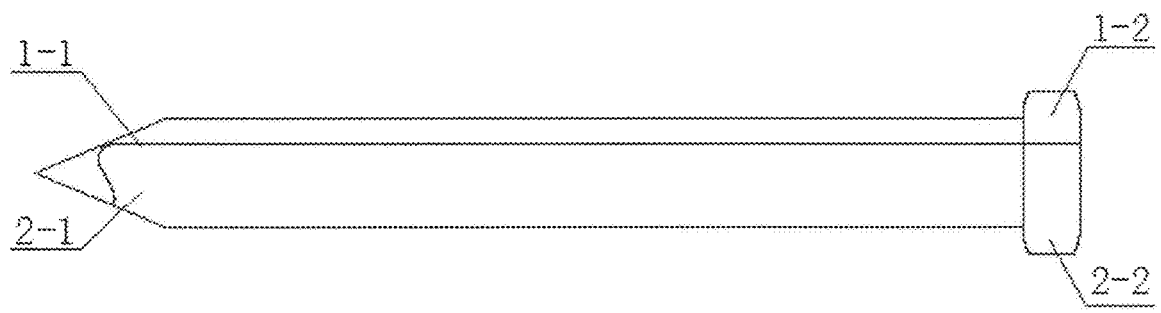
FIG. 18 is a top view of Embodiment 2 of the present invention.
Figure 19:
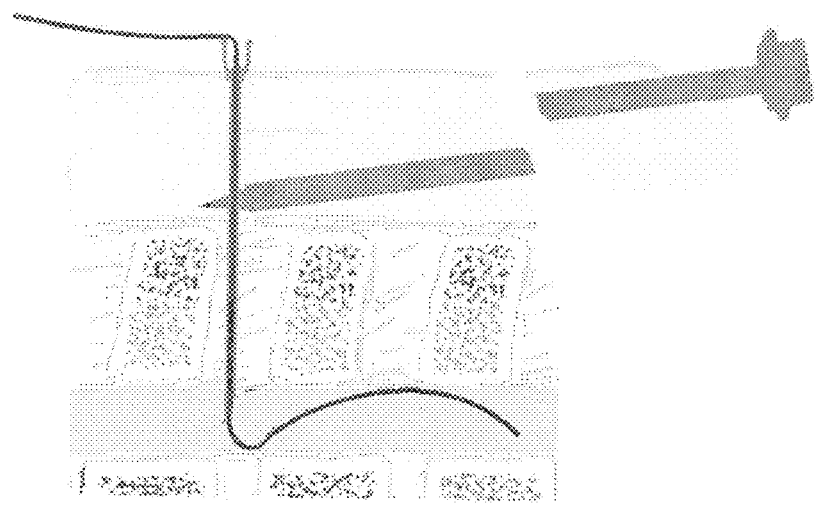
FIG. 19 is a schematic view showing a state in which the puncture needle is touched during actual use according to Embodiment 1 of the present invention.
Figure 20:
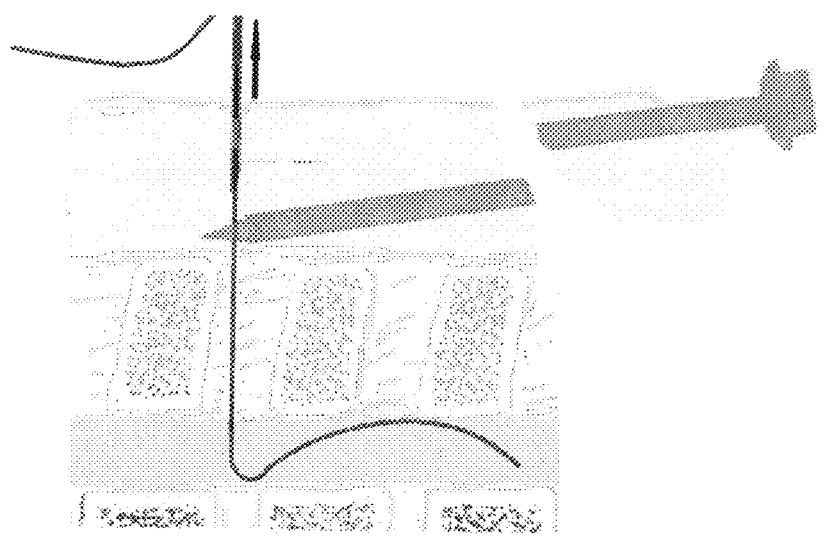
FIG. 20 is a schematic view showing a state in which the puncture needle is being retracted during actual use according to Embodiment 1 of the present invention.
Figure 21:
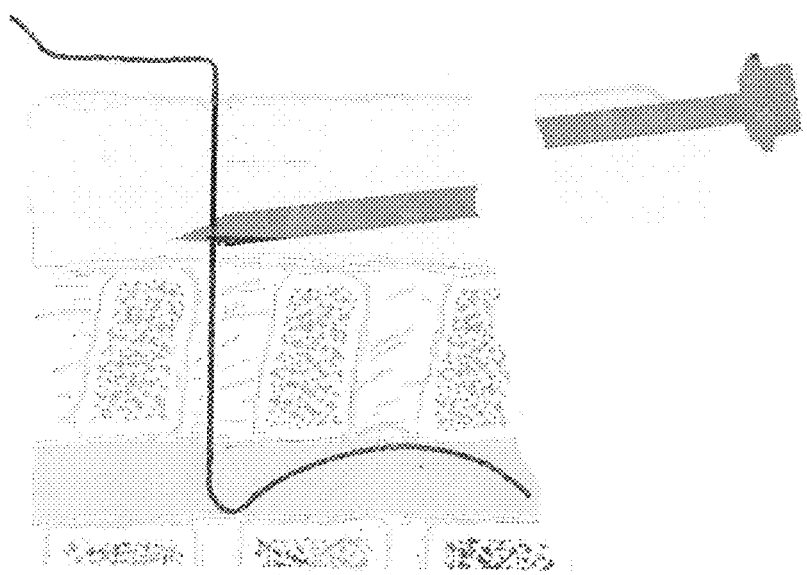
FIG. 21 is a schematic view showing a state in which the puncture needle has been completely retracted during actual use according to Embodiment 1 of the present invention.
Figure 22:
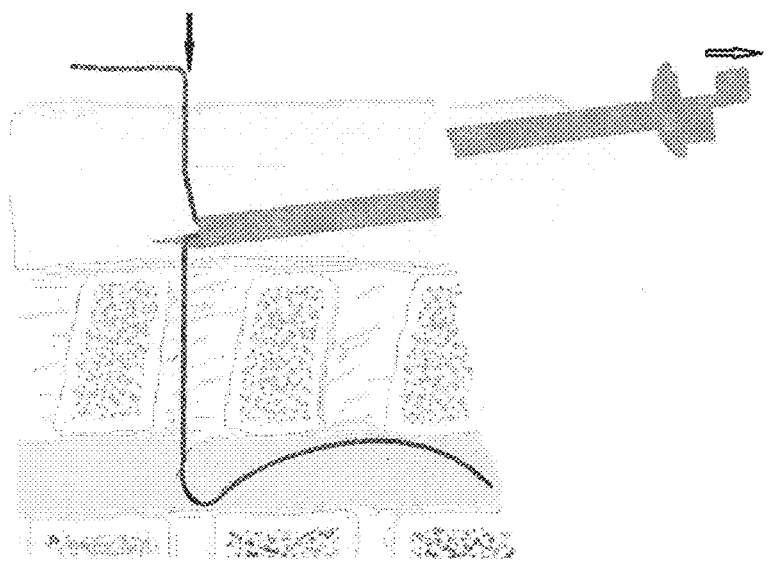
FIG. 22 is a schematic diagram showing a state in which the drainage tube starts to be pulled during actual use according to Embodiment 1 of the present invention.
Figure 23:
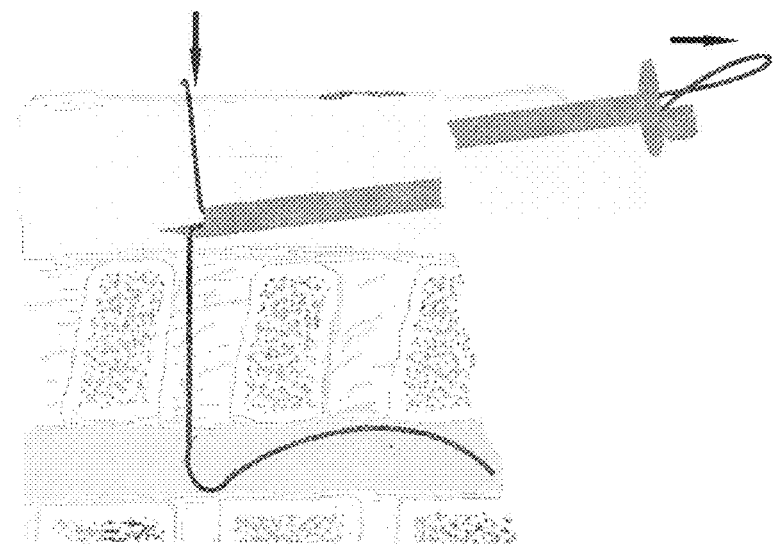
FIG. 23 is a schematic view showing a state in which part of the drainage tube is pulled out of the body during actual use according to Embodiment 1 of the present invention.
Figure 24:
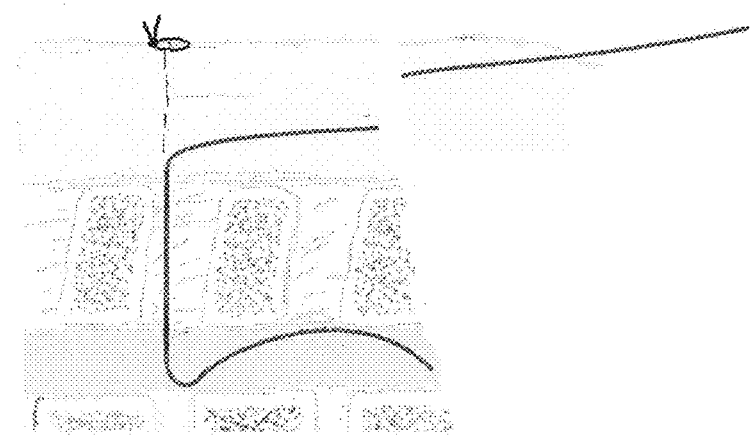

An apparatus for guiding post-puncture subcutaneous placement of an indwelling drainage tube is shown in FIGS. 17 and 18, including:

a first puncture needle core 1-1 and a second puncture needle core 2-1;

the front portion of the first puncture needle core 1-1 is a first tip 1-3, the first puncture needle core 1-1 has a first engagement portion 1-4, and the tail portion of the first puncture needle core is provided with a first handle 1-2;

the front end of the second puncture needle core 2-1 has a second engagement portion 2-3 that matches the first engagement portion of the first puncture needle core, and the tail portion of the second puncture needle core 2-1 is provided with a second handle 2-2.

As a preferred arrangement, the front ends of the first puncture needle core 1-1 and the second puncture needle core 2-1 form a semi-conical arrangement, so that the apparatus facilitates puncture.

The first engagement portion 1-4 of the first puncture needle core 1-1 is a composite curved surface, the second engagement portion 2-3 of the second puncture needle core 2-1 is also a composite curved surface, and the engagement portion between the first puncture needle core 1-1 and the second puncture needle core 2-1 can well accommodate a puncture needle 7 and a drainage tube 6 after being opened. After the second engagement portion 2-3 of the second puncture needle core 2-1 is closely attached to the first engagement portion of the first puncture needle core 1-1, the first puncture needle core 1-1 and the second puncture needle core 2-1 form an axisymmetric arrangement, the front end of which is semi-conical.

The surgical procedure of this apparatus is as follows:

After the puncture needle punctures successfully and the drainage tube 6 is placed to a sufficient depth through the puncture needle 7 (the placement depth of the drainage tube 6 is appropriately increased by 2-3 cm compared with the target depth), the puncture needle 7 and the drainage tube 6 are held still, and the apparatus punctures from a target position for leading the drainage tube 6 out to the puncture needle (the distance between two skin puncture holes is measured in advance to evaluate the puncture depth of the apparatus, and the subcutaneous length of the drainage tube); when the tips of the two needle cores touch the puncture needle 7, the two needle cores slide closely along the right side of the puncture needle, and the second puncture needle core 2-1 is retracted to enlarge the engagement gap between the first puncture needle core 1-1 and the second puncture needle core 2-1; when the front end of the guiding apparatus slides to the puncture needle, the jamming feeling is touched at an engagement opening; at this time, the second puncture needle core 2-1 is appropriately retracted to adjust the engagement gap between the first puncture needle core 1-1 and the second puncture needle core 2-1, so that the puncture needle is completely caught between the first puncture needle core 1-1 and the second puncture needle core 2-1. Subsequently, the puncture needle 7 is retracted while the depth of the drainage tube 6 is kept constant. If no jamming feeling is generated after the semi-conical front end of the guiding apparatus slides over the puncture needle, the position of the engagement opening may have been missed or the engagement opening between 1-1 and 2-1 is too small, the puncture needle core 2-1 may be appropriately retracted to enlarge the engagement opening, and the apparatus slides front and back close to the puncture needle.

Next, the first puncture needle core 1-1 is pulled backward, the drainage tube 6 is hooked and pulled by the hook-shaped engagement opening of the first puncture needle core 1-1, and the tail segment (part outside of the body) of the drainage tube 6 can be pushed into the body through the vertical puncture hole to reduce the pulling resistance of the first puncture needle core 1-1. After the first puncture needle core 1-1 pulls the drainage tube 2-3 cm away from the vertical puncture hole, the partial skin can be laterally pushed, the subcutaneous part of the head segment of the drainage tube 6 is pressed to fix the drainage tube 6 during the pulling process, and the vertical puncture hole on the skin should not be obstructed so as not to affect the pulling of the tail segment of the drainage tube into the body. After the drainage tube 6 is exposed through the side puncture hole, the tail segment of the drainage tube 6 is steadily pulled by hand and continuously pulled outward, and the pressing on the head segment of the drainage tube 6 is continuously kept at the vertical puncture hole to avoid shifting before the tail end of the drainage tube 6 is exposed to the outside of the body.

The apparatus provided in this embodiment is suitable for slim patients, and whether a suture line 8 is required for suturing is finally determined according to the condition of the puncture hole left by the vertical puncture. The state after the surgery can be referenced in FIG. 11.

With the above arrangement, the drainage tube 6 can be laterally extracted in the body after vertical puncture, which obviously extends the travel distance of the drainage tube in the body, changes the orientation of the drainage tube placed by the conventional method from perpendicular to approximately parallel to the skin, reduces the relative movement caused by the tension between the drainage tube and the skin and subcutaneous soft tissues during the activities such as turning over, increases the travel distance of the drainage tube in the subcutaneous soft tissues, and thickens the anti-infection barrier, thereby reduces the problems of around-drainage tube exudation, loosening of the drainage tube and even retrograde infection after tube placement by existing linear puncture. The care of patients with indwelling drainage tubes is improved, the chance of infection is reduced, the time of safe operation with the tube is ultimately prolonged, and the treatment effect is improved.

Described above are merely preferred embodiments of the present application, and the present application is not limited thereto. Various modifications and variations may be made to the present application for those skilled in the art. Any modification, equivalent substitution, improvement or the like made within the spirit and principle of the present application shall fall into the protection scope of the present application.

The invention claimed is:

1. An apparatus for guiding subcutaneous placement of a puncture indwelling drainage tube, the apparatus comprising:

a cannula in which a first puncture needle core, a second puncture needle core, a third puncture needle core, and a fourth puncture needle core are arranged, wherein:

a front end of the first puncture needle core is formed as a tip, the first puncture needle core having a first engagement portion, and a tail portion of the first puncture needle core includes a first handle, a front end of the second puncture needle core has a second engagement portion that matches the first engagement portion of the first puncture needle core, and a tail portion of the second puncture needle core includes a second handle, a front end of the third puncture needle core is formed as a tip, the third puncture needle core includes a third engagement portion, and a tail portion of the third puncture needle core having a third handle, a front end of the fourth puncture needle core has a fourth engagement portion that matches the third engagement portion of the third puncture needle core, and a tail portion of the fourth puncture needle core includes a fourth handle, the front ends of the four puncture needle cores all protrude from a front end of the cannula, and the four handles all protrude from a rear end of the cannula.

2. The apparatus according to claim 1, wherein the front end of the first puncture needle core, the front end of the second puncture needle core, the front end of the third puncture needle core, and the front end of the fourth puncture needle core form a conical arrangement.

3. The apparatus according to claim 1, wherein the cannula includes a holding portion.

4. The apparatus according to claim 1, wherein the first engagement portion includes: a first curved surface within the first puncture needle core, and the first curved surface is formed as a cambered edge extruded toward a side of the apparatus at the front end of the first puncture needle core, and a second curved surface on a side of the first puncture needle core, and the second curved surface is formed as a cambered edge extruded toward a side of the apparatus at the tail portion of the first puncture needle core.

5. The apparatus according to claim 4, wherein the second engagement portion includes: a third curved surface within the second puncture needle ore, the third curved surface is formed as a cambered edge extruded toward the side of the apparatus at the front end of the first puncture needle core and a fourth curved surface on a side of the second puncture needle core, and the fourth curved surface is formed as a cambered edge extruded toward the side of the apparatus at the tail portion of the first puncture needle core.

6. The apparatus according to claim 1, wherein the third engagement portion is formed by a planar arrangement, and thea main body of the third puncture needle core has a sector-annular-shaped cross section.

7. The apparatus according to claim 6, wherein the fourth engagement portion is formed by a planar arrangement, and a main body of the fourth puncture needle core has a sector-annular-shaped cross section.

8. The apparatus according to claim 7, wherein after the third puncture needle core and the fourth puncture needle core are integrally and closely attached to each other, a cross section of the main bodies of the third puncture needle core and the fourth puncture needle core form a D shape such that an inner side of the main body of the third puncture needle core and an inner side of the main body of the fourth puncture needle core together form a groove configured to accomodate the drainage tube.

9. The apparatus according to claim 1, wherein a side of the fourth puncture needle core at the side of the apparatus at the front end of the first puncture needle core has a guiding cambered surface at an inner edge of the fourth puncture needle core.

* * * * *